US011835700B2

(12) United States Patent
Guentert et al.

(10) Patent No.: US 11,835,700 B2
(45) Date of Patent: Dec. 5, 2023

(54) ILLUMINATION SYSTEM FOR A MICROSCOPE, SYSTEM, METHOD AND COMPUTER PROGRAM FOR A MICROSCOPE, AND MICROSCOPE SYSTEM

(71) Applicant: Leica Instruments (Singapore) Pte. Ltd., Singapore (SG)

(72) Inventors: Michael Guentert, Heerbrugg (CH); Ulrich Weiger, Montlingen (CH)

(73) Assignee: Leica Instruments (Singapore) Pte. Ltd., Singapore (SG)

( * ) Notice: Subject to any disclaimer, the term of this patent is extended or adjusted under 35 U.S.C. 154(b) by 5 days.

(21) Appl. No.: 17/195,567

(22) Filed: Mar. 8, 2021

(65) Prior Publication Data
US 2021/0286160 A1    Sep. 16, 2021

(30) Foreign Application Priority Data

Mar. 10, 2020   (DE) .................. 102020106499.3

(51) Int. Cl.
*G02B 21/36* (2006.01)
*G02B 21/06* (2006.01)
(Continued)

(52) U.S. Cl.
CPC ............ *G02B 21/06* (2013.01); *A61B 5/0071* (2013.01); *A61B 5/0077* (2013.01); *G02B 21/08* (2013.01);
(Continued)

(58) Field of Classification Search
CPC .... A61B 2017/00203; A61B 2090/309; A61B 2505/05; A61B 5/0035; A61B 5/0071;
(Continued)

(56) References Cited

U.S. PATENT DOCUMENTS

2009/0002813 A1    1/2009  Soon
2009/0153797 A1*   6/2009  Allon .................. A61B 3/12
                                                    362/11
(Continued)

FOREIGN PATENT DOCUMENTS

CN    102216674 A    10/2011
CN    102869919 A    1/2013
(Continued)

OTHER PUBLICATIONS

Wegerhoff Rainer et al: "Basics of Light Microscopy Imaging & Imaging Microscopy" (Jan. 20, 2011), XP055825048, Retrieved from the Internet: URL:https://www.embl.de/services/core_facilities/almf/events_ext/Basics_of_Light_microscopy_GIT.pdf [retrieved on Jul. 16, 2021], * sections "Colour temperature and white balance" and "Automated white balance adjustments" *.

*Primary Examiner* — Kathleen M Walsh
(74) *Attorney, Agent, or Firm* — 2SPL Patentanwälte PartG mbB; Kieran O'Leary

(57) ABSTRACT

Examples relate to a Light-Emitting Diode-based illumination system for a microscope, to a system, method and computer program for a microscope, and to a microscope system. The illumination system comprises one or more first LED-based light sources. The one or more first LED-based light sources are configured to emit light across a white light color spectrum. The illumination system comprises at least one optical filter. The at least one optical filter is arranged to filter the light emitted by the one or more first LED-based light sources. The illumination system comprises one or more second LED-based light sources. The one or more second LED-based light sources are configured to provide light having at least one peak at a wavelength that is tuned to an excitation wavelength of at least one fluorescent material.

14 Claims, 4 Drawing Sheets

(51) Int. Cl.
*G02B 21/08* (2006.01)
*G02B 21/16* (2006.01)
*A61B 5/00* (2006.01)
*H04N 23/74* (2023.01)

(52) U.S. Cl.
CPC ............ *G02B 21/16* (2013.01); *G02B 21/361* (2013.01); *G02B 21/365* (2013.01); *H04N 23/74* (2023.01)

(58) Field of Classification Search
CPC ....... A61B 5/0077; A61B 90/20; A61B 90/30; G02B 21/0012; G02B 21/06; G02B 21/08; G02B 21/082; G02B 21/16; G02B 21/361; G02B 21/365; H04N 5/2354
USPC .......................................................... 348/79
See application file for complete search history.

(56) References Cited

U.S. PATENT DOCUMENTS

| | | | |
|---|---|---|---|
| 2009/0201577 A1* | 8/2009 | LaPlante | G01N 21/6458 |
| | | | 313/501 |
| 2009/0236541 A1* | 9/2009 | Lomnes | A61B 1/0646 |
| | | | 250/362 |
| 2012/0085932 A1* | 4/2012 | Themelis | G01J 3/513 |
| | | | 356/407 |
| 2012/0326055 A1* | 12/2012 | Wilson | A61B 5/0059 |
| | | | 250/459.1 |
| 2016/0208998 A1 | 7/2016 | Greinke | |
| 2017/0167980 A1* | 6/2017 | Dimitriadis | A61B 3/14 |
| 2017/0202633 A1* | 7/2017 | Liu | G16H 40/63 |
| 2017/0209050 A1* | 7/2017 | Fengler | G01J 3/4406 |
| 2018/0177399 A1* | 6/2018 | Ntziachristos | A61B 1/00186 |
| 2019/0170647 A1 | 6/2019 | Ikenaga et al. | |
| 2020/0241270 A1* | 7/2020 | Stüven | G02B 21/0092 |
| 2021/0286159 A1* | 9/2021 | Guentert | G02B 21/08 |

FOREIGN PATENT DOCUMENTS

| | | | | |
|---|---|---|---|---|
| DE | 102009025127 A1 | | 12/2010 | |
| DE | 102014112285 A1 | | 3/2016 | |
| EP | 2359745 A1 | * | 8/2011 | ......... A61B 1/00009 |
| EP | 2359745 A1 | | 8/2011 | |
| JP | 2011070050 A | | 4/2011 | |
| JP | 2013057750 A | * | 3/2013 | |
| JP | 2013057750 A | | 3/2013 | |
| JP | 2014-003086 A | | 1/2014 | |
| WO | 2019158168 A1 | | 8/2019 | |

* cited by examiner

ILLUMINATION SYSTEM FOR A MICROSCOPE, SYSTEM, METHOD AND COMPUTER PROGRAM FOR A MICROSCOPE, AND MICROSCOPE SYSTEM

TECHNICAL FIELD

Examples relate to a Light-Emitting Diode-based illumination system for a microscope, to a system, method and computer program for a microscope, and to a microscope system.

BACKGROUND

In many microscope systems, Xenon-based illumination is used. To obtain light in different wavelength bands, the light of a Xenon-based light source is passed through a filter, e.g. through a filter wheel. This may lead to bulky, inefficient systems with high heat dissipation, which often rely on a fiber bundle from the stand to the carrier to provide the illumination at the carrier. Also, Xenon bulbs often have a limited lifetime, so they may be replaced fre-quently, requiring a backup light source to avoid situations in which the light source fails during a critical situation, e.g. during surgery. Also, such a setup is inflexible, as the Xenon light source is used for both white light reflectance illumination and for fluorescence excitation, albeit using different filter wheels.

SUMMARY

There may be a desire for an improved illumination system for a microscope that overcomes the above-mentioned drawbacks.

This desire is addressed by the subject-matter of the independent claims.

Embodiments of the present disclosure are based on the finding that it may be desirable to control the spectra for white light and fluorescence excitation independent from each other. Such a control may be achieved by using Light-Emitting Diode (LED) based light sources, which may be tuned or configured to specific wavelength bands, while using less energy, and thus producing less heat, than Xenon-based illumination systems. To support both lighting in the white light spectrum and in a spectrum for fluorescence excitation, two sets of light sources may be included, one for providing white light, and one for providing light having a peak at a wavelength that is tuned to an excitation wavelength of at least one fluorescent material.

Embodiments of the present disclosure provide a LED-based illumination system for a microscope. The illumination system comprises one or more first LED-based light sources. The one or more first LED-based light sources are configured to emit light across a white light color spectrum. The illumination system comprises at least one optical filter. The at least one optical filter is arranged to filter the light emitted by the one or more first LED-based light sources. The illumination system comprises one or more second LED-based light sources.

The one or more second LED-based light sources are configured to provide light having at least one peak at a wavelength that is tuned to an excitation wavelength of at least one fluorescent material. By using LED-based light sources, the energy consumption, and thus the heat dissipation may be reduced. Furthermore, as LED-based light sources are compact, they can be included near the objective of the microscope, instead of using fiber channels to trans-
port the light to the carrier. The two groups of light sources can be used to independently control the illumination for white light and fluorescence excitation. The filter may be used to block or attenuate light at wavelengths that coincide with an emission spectrum of the fluorescent material, so the emissions of the fluorescent material can be distinguished within image data while the white light LED sources are active.

For example, the one or more second LED-based light sources may be configured to emit light having a peak at one or more of between 390 nm and 420 nm, between 460 nm and 500 nm, and between 780 nm and 810 nm. These wavelengths are excitation wavelengths of common fluorescent materials.

The at least one optical filter may be configured to attenuate or block light having a wave-length that coincides with at least one fluorescence emission wavelength of the at least one fluorescent material. This may enable distinguishing the emissions of the fluorescent material while the white light LED sources are active.

For example, the at least one optical filter may be configured to attenuate or block light within a wavelength band between 490 nm and 560 nm. Additionally or alternatively, the at least one optical filter may be configured to attenuate or block light within a wavelength band between 610 nm and 660 nm. These wavelength bands are emission wavelengths of common fluorescent materials.

In some embodiments, the illumination system comprises one or more third LED-based light sources. The one or more third LED-based light sources may be configured to emit light across the white light color spectrum. These additional light sources may be used to provide white light that is not filtered by the at least one optical filter.

The illumination system may comprise two or more first LED-based light sources and two or more second LED-based light sources, for example. Having two or more light sources of each provides both a degree of redundancy and also enables positioning the light sources at either side of the objective of the microscope.

For example, at least a subset of the one or more second LED-based light sources are configured to provide light having at least one peak at a wavelength that is tuned to an excitation wavelength of the at least one fluorescent material without using a filter to limit the emitted light to the at least one peak. This may enable a more compact construction of the illumination system, by foregoing the need for a filter.

In some embodiments, the illumination system may comprise a (e.g. at least one) second optical filter that is arranged to filter the light emitted by at least a subset of the one or more second LED-based light sources. This may enable a use of more generic light sources, e.g. if LED-based light sources having a specific peak are not available, and/or a later adaptation of the peak or peaks of the one or more second light sources.

The illumination system may further comprise one or more processors configured to control the one or more first and the one or more second LED-based light sources independent from each other. This may enable an independent control of the white light and fluorescence lighting of the microscope.

Each LED-based light source may be configured to emit light towards a sample to be observed via the microscope. For example, each LED-based light source may be configured to emit the light towards the sample through an optical concentration element. The optical concentration element may be a compound parabolic concentrator. Through the optical concentration element, the illumination may be directed at the sample, reducing an amount of energy re-quired for the light sources.

For example, the at least one fluorescent material may be at least one fluorescent dye. Fluorescent dyes are often used in connection with microscopes, e.g. in bio-laboratory or surgical environments.

Embodiments of the present disclosure further provide a system for a microscope. The system comprises one or more processors and one or more storage devices. The system is configured to obtain image data of an optical imaging sensor of the microscope. The image data represents light reflected by a sample that is illuminated by one or more LED-based light sources. The light emitted by the one or more LED-based light sources is filtered such that light having a wavelength that coincides with at least one fluorescence emission wavelength of the at least one fluorescent material is attenuated or blocked. The system is configured to process the image data to generate processed image data. A portion of the processed image data that represents light having a wavelength that coincides with the at least one fluorescence emission wavelength of the at least one fluorescent material is generated based on the image data. The system is configured to output the processed image data. For example, the system may comprise the illumination system introduced above. The image data may represent light reflected by the sample that is illuminated by the one or more first LED-based light sources of the illumination system. Using the system, processed image data may be output that shows a reflectance image across the white light spectrum, based on an illumination that excludes some parts of the spectrum to account for fluorescence imaging.

Embodiments of the present disclosure further provide a method for a microscope. The method comprises obtaining image data of an optical imaging sensor of the microscope. The image data represents light reflected by a sample that is illuminated by one or more LED-based light sources. The light emitted by the one or more LED-based light sources is filtered such that light having a wavelength that coincides with at least one fluorescence emission wavelength of at least one fluorescent material is attenuated or blocked. The method comprises processing the image data to generate processed image data, wherein a portion of the processed image data representing light having a wavelength that coincides with the at least one fluorescence emission wavelength of the at least one fluorescent material is generated based on the image data. The method further comprises outputting the processed image data.

Embodiments of the present disclosure further provide a computer program with a program code for performing the method, when the computer program is executed on a processor.

Embodiments of the present disclosure further provide a microscope system comprising a microscope and the illumination system introduced above. Each LED-based light source of the illumination system is configured to emit light towards a sample to be observed via the microscope. Each LED-based light source is arranged adjacent to an objective of the microscope. Thus, fiber channels for transporting the light from the base of the microscope system to the carrier may be omitted.

In various embodiments, the illumination system comprises two or more first LED-based light sources and two or more second LED-based light sources. At least one of the two or more first LED-based light sources and at least one of the two or more second LED-based light sources may be arranged at a first side of the objective. At least one of the two or more first LED-based light sources and at least one of the two or more second LED-based light sources may be arranged at a second side of the objective. Having at least two light sources of each provides both a degree of redundancy and also enables positioning the light sources at either side of the objective of the microscope.

SHORT DESCRIPTION OF THE FIGURES

Some examples of apparatuses and/or methods will be described in the following by way of example only, and with reference to the accompanying figures, in which FIG. 1a shows a schematic diagram of an embodiment of an illumination system for a microscope and of a system for a microscope;

DETAILED DESCRIPTION

Various examples will now be described more fully with reference to the accompanying draw-ings in which some examples are illustrated. In the figures, the thicknesses of lines, layers and/or regions may be exaggerated for clarity.

Figure 1A:
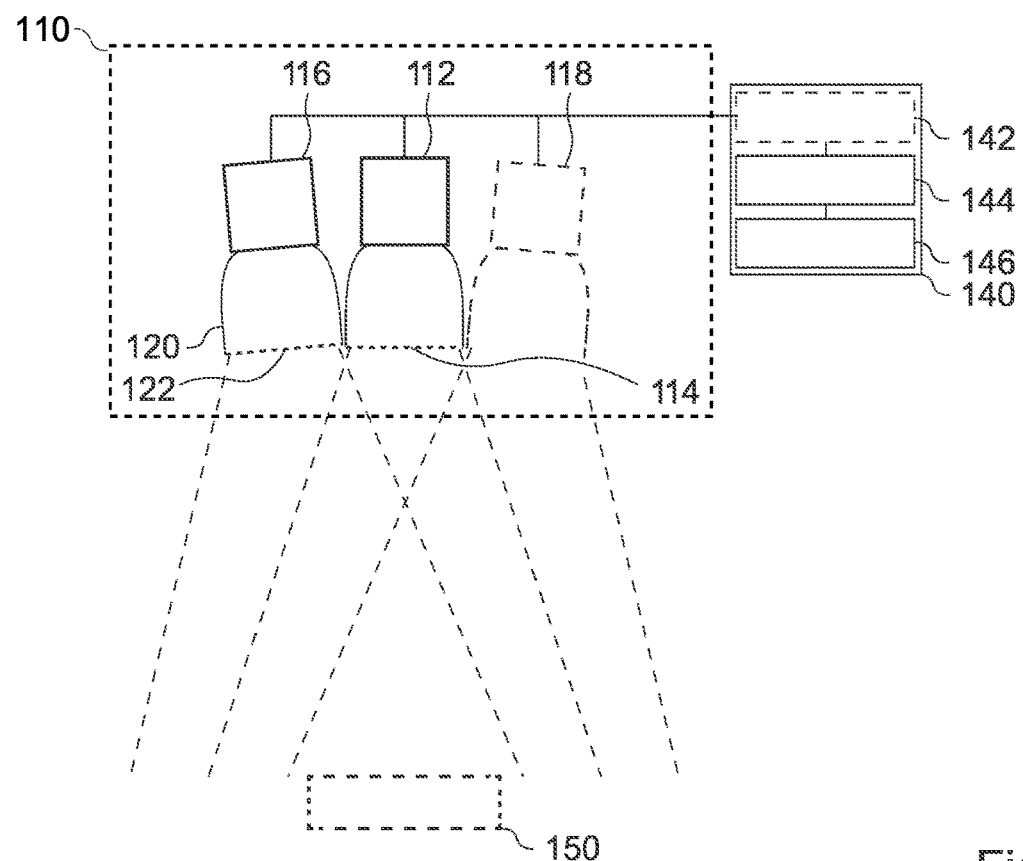
FIG. 1b shows a schematic diagram of an embodiment of a surgical microscope system.

FIG. 1a shows a schematic diagram of an embodiment of an illumination system 110 for a microscope. The illumination system 110 is an LED-based illumination system 110 that is suitable for microscope 130 of FIG. 1b. The illumination system comprises one or more first LED-based light sources 112. The one or more first LED-based light sources are configured to emit light across a white light color spectrum. The illumination system comprises at least one optical filter 114. The at least one optical filter is arranged to filter the light emitted by the one or more first LED-based light sources. The illumination system comprises one or more second LED-based light sources 116. The one or more second LED-based light sources are configured to provide light having at least one peak at a wavelength that is tuned to an excitation wavelength of at least one fluorescent material. Each LED-based light source 112; 116 (and optionally 118) may be configured to emit light towards a sample 150 to be observed via the microscope 130.

Figure 1B:
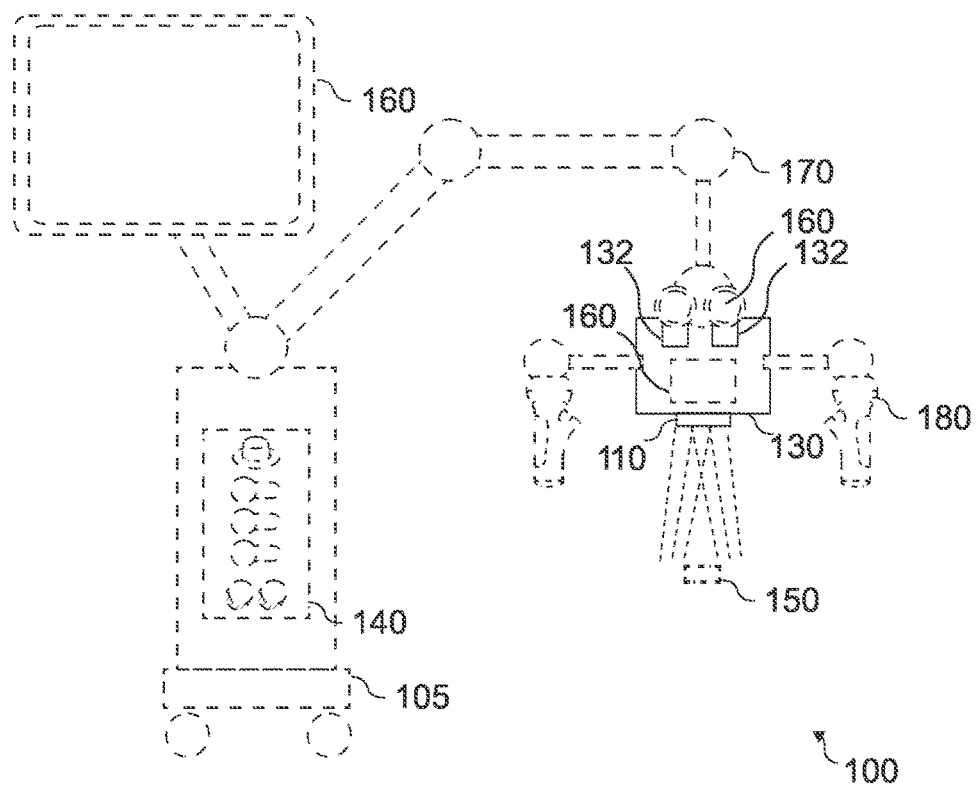
Figure 3A:
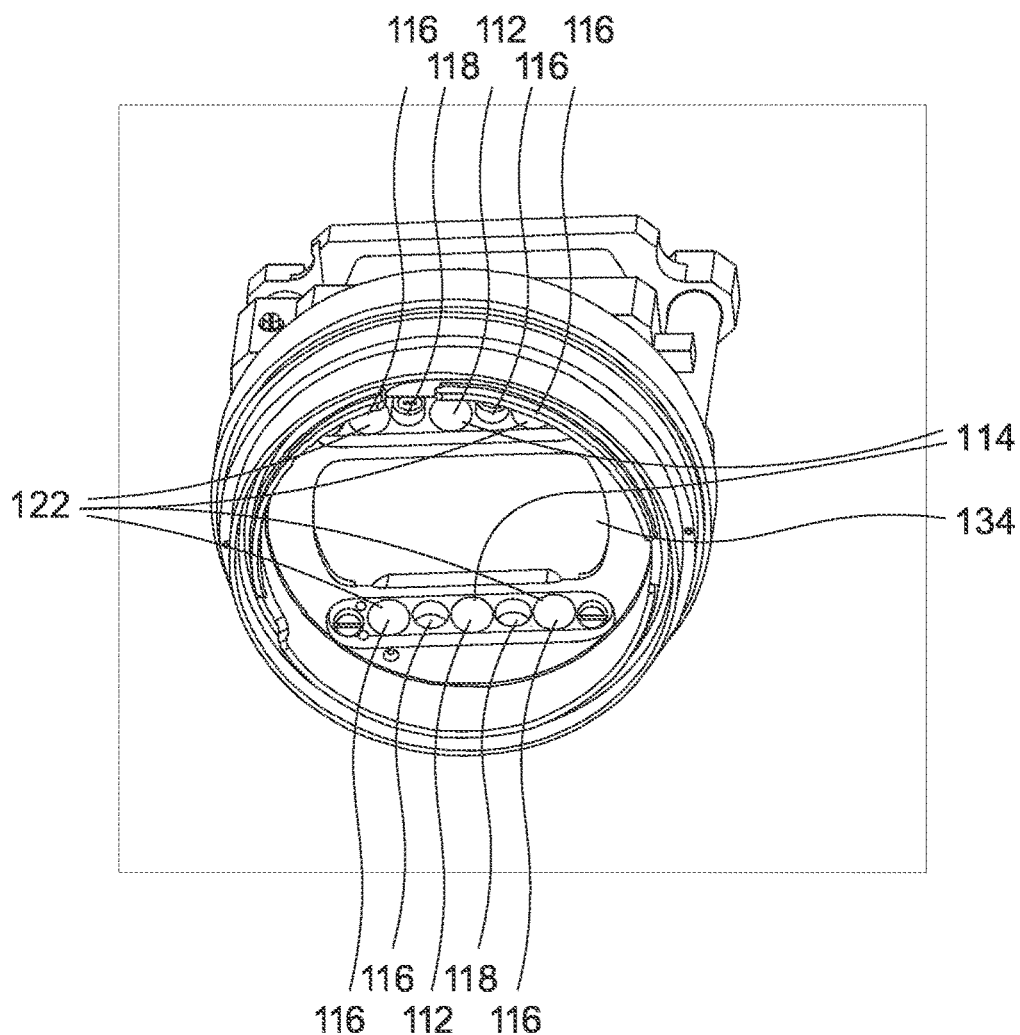
FIGS. 3a and 3b show schematic diagrams of embodiments of a microscope system.
Figure 3B:
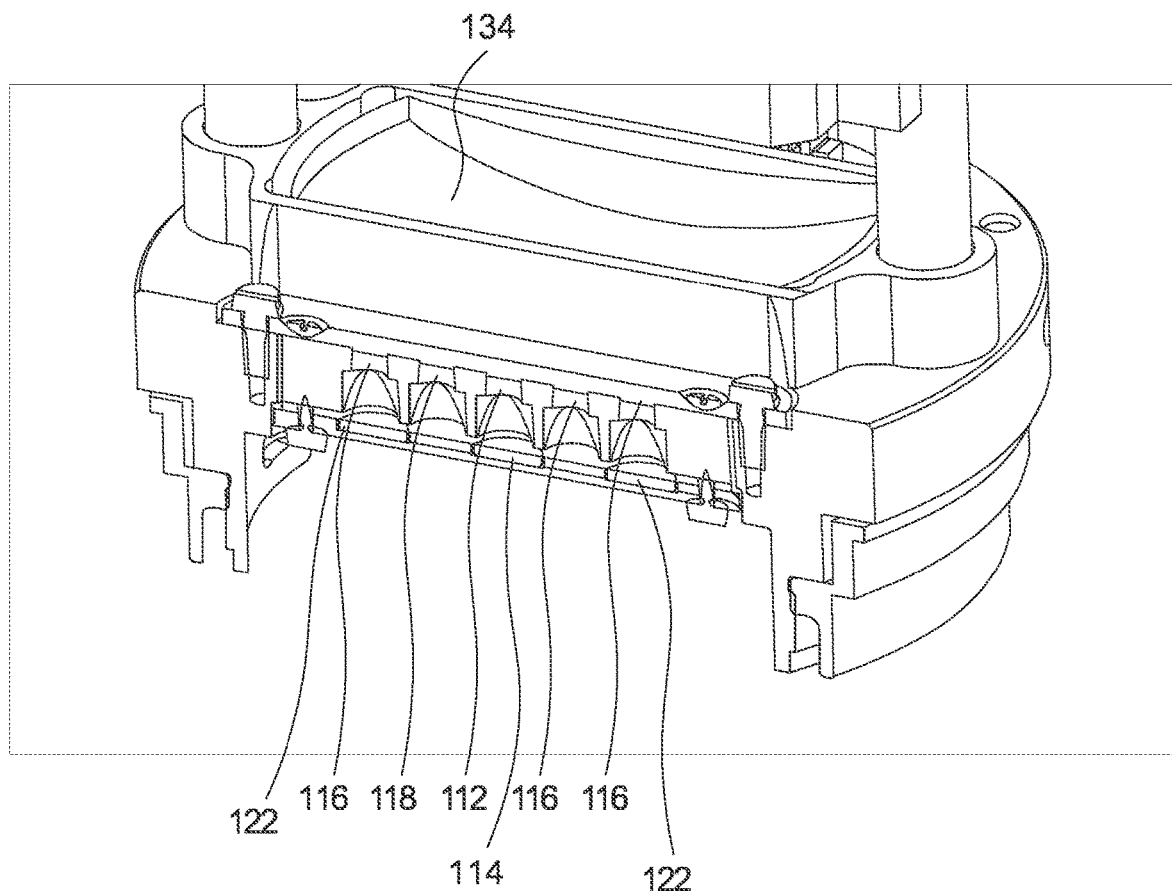

At least some aspects of FIG. 1a relate to an illumination system 110 for a microscope. In general, a microscope is an optical instrument that is suitable for examining objects that are potentially too small to be examined by the human eye (alone). For example, a microscope may provide an optical magnification of a sample. In modern microscopes, the optical magnification is often provided for a camera or an imaging sensor, such as an optical imaging sensor 132 of the microscope 130 that is shown in FIG. 1b. Alternatively, a purely optical approach may be taken. The microscope 130 may further comprise one or more optical magnification components that are used to magnify a view on the sample, such as an objective (i.e. lens) 134 that is shown in FIGS. 3a and 3b. In the context of this application, the term "(surgical) microscope system" is used, in order to cover the portions of the system that are not part of the actual microscope (which comprises optical components), but which are used in conjunction with the microscope, such as the system 140 or the illumination system 110.

There are a variety of different types of microscopes. If the microscope is used in the medical or biological fields, the sample 150 being viewed through the microscope may be a sample of organic tissue, e.g. arranged within a petri dish or present in a part of a body of a patient. For example, the microscope system 100 may be a microscope system for use in a laboratory, e.g. a microscope that may be used to examine the sample of organic tissue in a petri dish. Alternatively, the microscope 130 may be part of a surgical microscope system 100, e.g. a microscope to be used during a surgical procedure. Such a system is shown in FIG. 1b, for example. Although embodiments are described in connection with a microscope, they may also be applied, in a more general manner, to any optical device.

In microscope systems, illumination systems are generally used to illuminate the sample 150, e.g. a sample on a sample stage (in case of a laboratory microscope), or a patient on an oper-ating table. Consequently, the light sources 112 and 116 (and, as introduced below, 118) may be configured to emit light towards the sample 150 to be observed via the microscope 130. In other words, the light emitted by the light sources may be directed at the sample 150, e.g. at the sample stage, or towards the patient. To avoid an overly wide beam angle of the light source, optical concentration elements may be used to direct the light towards the sample. In other words, each LED-based light source may be configured to emit the light towards the sample through an optical concentration element 120 (as further shown in FIG. 1a). In general, different kinds of optical concentration elements 120 may be used, such as lenses, light guides, or parabolic concentrators. In the embodiment shown in FIG. 1a, and later in FIGS. 3a and 3b, compound parabolic concentrators are used. In other words, the optical concentration element may be a compound parabolic concentrator (CPC), e.g. Total Internal Reflection (TIR)-based CPC. Compound parabolic concentrators are optical elements, having a hollow and parabolic shape, that are suitable for collecting and concentrating light from light sources, and that yield a pre-defined maximal angle at which the light is emitted from the compound parabolic concentrator. As shown in FIGS. 1a and 3a/3b, each light source may be coupled with a compound parabolic concentrator, and the light of the light sources may be concentrated by the compound parabolic concentrator coupled with the light sources.

In general, the light sources being used in embodiments of the present disclosure are LED-based light sources. In general, an LED-based light source may comprise an LED, e.g. a sur-face mounted LED (i.e. a SMD LED), and a connection structure for electrically connecting the LED to an energy source. LEDs are usually connected to driver circuit (usually an integrated circuit) that is configured to supply the LED with energy, i.e. with an electric current. In some embodiments, each light source may comprise a corresponding driver circuit. Alternatively, a common driver circuit may be used to supply (all of) the LEDs with energy. In any case, the driver circuit may be used to drive the LEDs at full intensity. Alternatively or additionally, the driver may be capable of driving the LEDs with less than full intensity, which is denoted "dimming". In general, in illumination systems for microscopes, different levels of light intensity may be desired, so the light sources may be dimmable, i.e. a driver circuit of the light sources may be capable of driving the LEDs with less than full intensity, e.g. in response to a control signal from a control device. Various approaches may be used for the dimming, such as electric current-based dimming, or pulse-width modulation-based dimming. For example, the system 140, e.g. one or more processors 144 of the system 144, also shown in FIG. 1a, may be configured to control the light sources. As individual light sources are being used, the light sources may be controlled independently from each other (if each light source has their own driver circuit), or at least in groups (e.g. if the first and second light sources have different driver circuits, or are independently controllable via a single driver circuit). Accordingly, the one or more processors 144 (or, more generally, the system 140) may be configured to control the one or more first and the one or more second LED-based light sources independent from each other.

The illumination system comprises different groups (or sets) of light sources. For example, the illumination system comprises a first group or set of light sources comprising the one or more first LED-based light sources 112, and a second group or set of light sources comprising the one or more second LED-based light sources 116. In some embodiments, as also shown in FIG. 1a, the illumination system may even comprise a third group or set of light sources comprising one or more third LED-based light sources 118.

In general, the light sources (or groups/sets) of light sources may be distinguished by the light spectra they emit, or by the light spectra they emit after being filtered by one of the filters. For example, the one or more first LED-based light sources are configured to emit light across the white light color spectrum. In other words, the one or more first LED-based light sources may be configured to emit light at a continuous wavelength band that continually spans at least 90% of the wavelength band between 380 nm and 740 nm. The one or more first LED-based light sources may be broad-band light sources emitting light in a continuous wavelength band spanning at least a 300 nm range. In more generic terms, the one or more first LED-based light sources may be denoted "white light" LEDs, i.e. LEDs that emit light that is perceived as being "white light" due to the inclusion of a wide wavelength band.

The one or more second LED-based light sources are different—they emit light having at least one peak at a wavelength that is tuned to an excitation wavelength of at least one fluorescent material. Accordingly, the one or more second LED-based light sources may be denoted "fluorescence excitation light sources". In other words, the one or more second LED-based light sources may be narrow-band light sources (i.e. they emit at one or multiple wave-length bands each spanning less than a 100 nm wavelength range). This may be achieved using different approaches. For example, the light sources may be light sources that only emit light in a narrow band, without using a filter. In other words, at least a subset of the one or more second LED-based light sources may be configured to provide light having at least one peak at a wavelength that is tuned to an excitation wavelength of the at least one fluorescent material without using a filter to limit the emitted light to the at least one peak. In other words, at least a subset of the one or more second LED-based light sources may comprise LEDs that are configured to emit light in a narrow band (i.e. less than a 100 nm wavelength range, or less than a 50 nm wavelength range). Alternatively or additionally, filters may be used with a subset of the one or more second LED-based light sources. In other words, as further shown in FIG. 1a, the illumination system (e.g. at least a subset of the one or more second LED-based light sources) may comprise a second optical filter 122 (e.g. at least one second optical filter 122), arranged to filter the light emitted by at least a subset of the one or more second LED-based light sources. For example, the second filter may be configured to limit the light emitted by at least a subset of the one or more second LED-based light sources to the at least one peak at a wavelength that is tuned to an excitation wavelength of the at least one fluorescent material. In some embodiments, the two approaches may be combined—for a subset of the fluorescent materials, a light source without a filter may be used (as a sufficiently narrow-band light source is available), for another subset of the fluorescent materials, a filter may be used to (further) limit the emitted wavelengths. For example, In the context of this application, the term "light having at least one peak at a wavelength that is tuned to an excitation wavelength of at least one fluorescent material" may be understood as the light having its highest intensity at a wavelength or wavelength band that intersects with an excitation wavelength or wave-length band of at least one fluorescent material, with light at other wavelengths being emitted at an intensity that is at most 80% (or at most 50%, at most 20%, at most 10%) of the highest intensity.

In general, the light emitted by the one or more second LED-based light sources is tuned to the excitation wavelength/wavelengths of at least one fluorescent material. Fluorescent materials are often used in microscopy to highlight a portion of a tissue or a blood vessel that has been previously marked using a fluorescent material. For example, a fluorescent dye, such as fluorescein, indocyanine green (ICG) or 5-ALA (5-aminolevulinic acid) may be used to mark the tissue or vessel. In other words, the at least one fluorescent material may be at least one fluorescent dye. Fluorescent materials are materials that are excited by light at one wave-length/in a first wavelength band (i.e. their "excitation wavelength"), but emit light in another wavelength band (i.e. their "emission wavelength"). Thus, the one or more second LED-based light sources emit light that has its peak at the excitation wavelength/wavelengths of the fluorescent materials. For typically used fluorescent dyes, the excitation wavelength may be between 390 nm and 420 nm, between 460 nm and 500 nm, or between 780 nm and 810 nm. For example, in an example shown in FIGS. 3a and 3b, three different second LED-based light sources are used, having their respective peaks at 405 nm, 480 nm and 788 nm. Accordingly, the one or more second LED-based light sources may be configured to emit light having a peak at one or more of between 390 nm and 420 nm, between 460 nm and 500 nm, and between 780 nm and 810 nm. For example, different light sources of the one or more second LED-based light sources may emit light having a peak at different excitation wave-length/wavelengths of different fluorescent materials. In this case, these different light sources may be controlled mutually independently from each other by the system 140/one or more processors 144.

Figure 4:
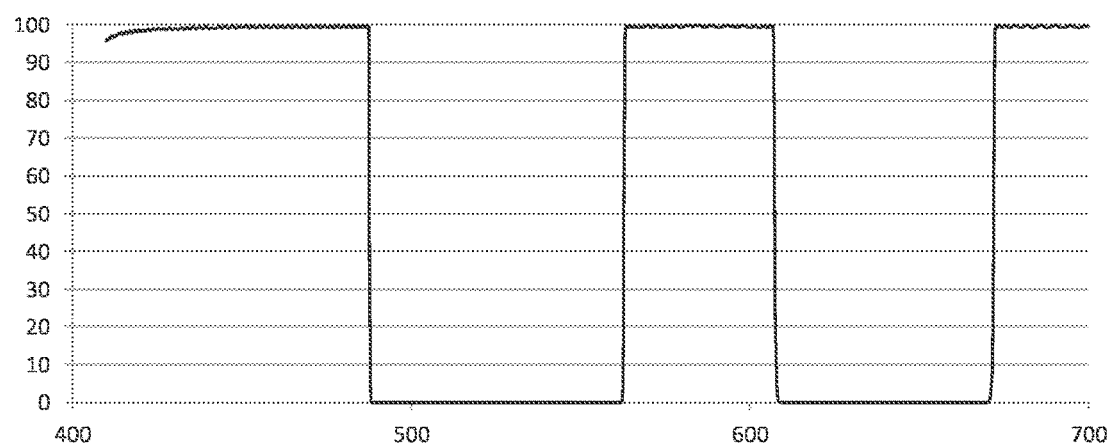
FIG. 4 shows a diagram of a transmission of a band pass filter for filtering white light.

To avoid the one or more first LED-based light sources drowning out the light emitted by the fluorescent materials, light in the emission wavelength bands of the at least one fluorescent material may be filtered out from the light emitted by the one or more LED-based light sources. In other words, the at least one optical filter may be configured to attenuate or block light having a wavelength that coincides with at least one fluorescence emission wavelength of the at least one fluorescent material. Accordingly, the at least one optical filter may be configured to attenuate or block light within a wavelength band between 490 nm and 560 nm, and/or the at least one optical filter may be configured to attenuate or block light within a wavelength band between 610 nm and 660 nm. The wavelength bands between 490 nm and 560 nm, and between 610 nm and 660 nm may be emission wavelength bands of common fluorescent dyes. In consequence, the first and second sets of light sources may be used concur-rently, and the fluorescence emissions may still be visible, as the corresponding portions of the light emitted by the first group or set is filtered out. Accordingly, the at least one optical filter may be arranged in a light path between the one or more first LED-based light sources and a sample 150 to be perceived through the microscope. Furthermore, the at least one optical filter may be arranged to filter the light emitted by each of the one or more first LED-based light sources, i.e. none of the light emitted by the one or more first lights sources may bypass the at least one optical filter. For example, the at least one optical filter may be a bandpass filter, e.g. a bandpass filter with filter characteristics as shown in FIG. 4.

In some embodiments, as further shown in FIG. 1a, a third set or group LED-based light sources 118 may be used. In other words, the illumination system 110 may comprise one or more third LED-based light sources 118. The one or more third LED-based light sources may be configured to emit light across the white light color spectrum. Accordingly, the one or more third LED-based light sources may be implemented similar to the one or more first LED-based light sources. The light emitted by third set or group LED-based light sources, however, might not be filtered by the at least one optical filter. Consequently, light emitted by the one or more third LED-based light sources may reach the sample across the (entire) white light color spectrum.

To achieve redundancy and an even illumination of the sample, multiple light sources of each of the groups or sets light sources may be included in the illumination system. For example, the illumination system may comprise two or more first LED-based light sources and two or more second LED-based light sources (and, optionally, two or more third LED-based light sources). In some embodiments, even higher numbers may be used, e.g. four or six first LED-based light sources, four or six first LED-based light sources, and/or four or six third LED-based light sources. In FIGS. 3a and 3b, an example is shown where two first LED-based light sources, six second LED-based light sources and two third LED-based light sources are used. The light sources of each group or set may be arranged at either side of an objective 134 of the microscope 130. For example, at least one LED-based light source for each wavelength band (e.g. one first LED-based light source, one third LED-based light source, and three second LED-based light sources for three excitation wavelengths of three fluorescent materials, as shown in FIGS. 3a and 3b) may be arranged at either side of the objective. In other words, at least one of the two or more first LED-based light sources and at least one of the two or more second LED-based light sources (and optionally at least one of the two or more third LED-based light sources) may be arranged at a first side of the objective, and at least one of the two or more first LED-based light sources and at least one of the two or more second LED-based light sources (and optionally at least one of the two or more third LED-based light sources) may be arranged at a second side of the objective. For example, the first side and the second side may be opposing sides relative to the objective of the microscope 130.

The filters being employed with the one or more first LED-based light sources lead to an illumination of the sample (e.g. of the surgical site) that is non-uniform across the white-light spectrum. This non-uniformity may be compensated in image-processing, e.g. by the system 140. FIG. 1a further shows a schematic diagram of an embodiment of the system 140 that is suitable for the microscope 130. FIG. 1a further shows a system comprising the illumination system 110 and the system 140. The system 140 comprises one or more processors 144 and one or more storage devices 146. Optionally, the system 140 comprises an interface 142. The one or more processors 144 are coupled to the interface 142 and to the one or more storage devices 146. In general, the one or more processors may be configured to provide the func-tionality of the system 140, e.g. in conjunction with the one or more storage devices and/or in conjunction with the interface.

For example, the system is configured to obtain image data of an optical imaging sensor 132 of the microscope 130 (e.g. via the interface 142). Accordingly, the system 140 may be coupled to the microscope 130, e.g. via the interface 142. The image data represents light reflected by a sample that is illuminated by one or more LED-based light sources. The light emitted by the one or more LED-based light sources is filtered such that light having a wavelength that coincides with at least one fluorescence emission wavelength of the at least one fluorescent material is attenuated or blocked. The system is configured to process the image data to generate processed image data. A portion of the processed image data representing light having a wavelength that coincides with the at least one fluorescence emission wavelength of the at least one fluorescent material is generated based on the image data. The system is configured to output the processed image data (e.g. via the interface 142 or via the one or more storage devices 146).

In general, the system 140 may be used with any illumination system for a microscope that is configured to provide light that is filtered such that light having a wavelength that coincides with at least one fluorescence emission wavelength of the at least one fluorescent material is attenuated or blocked. In particular, however, the light may be provided by the illumination system 110. Accordingly, the system 140 may further comprise the illumination system 110, or the system 140 may be used in conjunction with the illumination system 110. In this case, the image data may represent light reflected by the sample that is illuminated by the one or more first LED-based light sources 112 of the illumination system 110. The filtering of the light has the effect, that reflections of the respective portions of the white light spectrum are not (or to a lesser degree, in case of attenuation) represented by the image data.

In some embodiments, the system 140, e.g. the one or more processors 144 may be configured to control the one or more first and the one or more second LED-based light sources. Accordingly, the system 140, e.g. the one or more processors 144, may be coupled to the illumination system 110, e.g. via the interface 142.

For example, the optical imaging sensor 132 may comprise or be APS (Active Pixel Sensor)—or a CCD (Charge-Coupled-Device)-based imaging sensors. For example, in APS-based imaging sensors, light is recorded at each pixel using a photo-detector and an active amplifier of the pixel. APS-based imaging sensors are often based on CMOS (Complementary Metal-Oxide-Semiconductor) or S-CMOS (Scientific CMOS) technology. In CCD-based imaging sensors, incoming photons are converted into electron charges at a semiconductor-oxide interface, which are subsequently moved between capacitive bins in the imaging sensors by a control circuitry of the imaging sensors to perform the imaging. The system is configured to obtain (i.e. receive or read out) the image data from the optical imaging sensor 132. The image data may be obtained by receiving the image data from the optical imaging sensor 132 (e.g. via the interface 142), by reading the image data out from a memory of the optical imaging sensor (e.g. via the interface 142), or by reading the image data from a storage device 146 of the system 140, e.g. after the image data has been written to the storage device 146 by the optical imaging sensor 132 or by another system or processor.

The image data represents light reflected by a sample that is illuminated by one or more LED-based light sources (e.g. by the one or more first LED-based light sources 112 of FIG. 1*a*). The light emitted by the one or more LED-based light sources is filtered such that light having a wavelength that coincides with at least one fluorescence emission wavelength of the at least one fluorescent material is attenuated or blocked (e.g. by the at least one optical filter 114).

The system is configured to process the image data to generate processed image data. In other words, the system may be configured to perform image processing on the image data. For example, the image processing may be performed to compensate for (or reduce the effects of) the non-uniformity of the illumination over the white light spectrum. For example, the system may be configured to reconstruct the portion of the processed image data representing light having a wavelength that coincides with the at least one fluorescence emission wavelength of the at least one fluorescent material, e.g. by using information from adjacent wavelength bands. For example, if light in one of the wavelength bands between 490 nm and 560 nm, and between 610 and 660 nm is blocked or attenuated in the illumination of the sample, light from adjacent wavelength bands (e.g. up to 490 nm, between 560 nm and 610 nm, and from 660 nm up) may be used to reconstruct the light that has been blocked or attenuated by the filter. In other words, the system may be configured to reconstruct the light that is attenuated or blocked, i.e. the light having a wavelength that coincides with at least one fluorescence emission wavelength of the at least one fluorescent material. For example, the system may be configured to apply a transformation function that performs a transformation between the image data (which may be raw image data, i.e. comprise the sensor output of the optical imaging sensor) and the processed image data, with the transformation function mapping the wave-length bands outside the at least one fluorescence emission wavelength to the (entire) white light spectrum. Thus, a portion of the processed image data representing light having a wave-length that coincides with the at least one fluorescence emission wavelength of the at least one fluorescent material is generated (i.e. reconstructed) based on the image data.

In addition, the system may be used to control the LED-based light sources. In other words, the illumination system may comprise one or more processors 144 (e.g. the system 140) configured to control the one or more first and the one or more second LED-based light sources independent from each other. For example, at least one of an on-off-state and a light intensity may be controlled independently for the one or more first and the one or more second LED-based light sources (and optionally for the one or more third LED-based light sources). More precisely, an on-off-state and/or a light intensity for the one or more first LED-based light sources may be controlled independently from an on-off-state and/or a light intensity for the one or more second LED-based light sources (and optionally from an on-off-state and/or a light intensity for the one or more third LED-based light sources). In some embodiments, each LED-based light source may be controlled independently from each other (or at least independently from LED-based light sources of other groups or sets).

The above illumination system 110 and system 140 are suitable for use with the microscope 130, e.g. in a microscope system 100. FIG. 1*b* shows a schematic diagram of an embodiment of a surgical microscope system 100 that comprises the microscope 130 and the illumination system 110. Each LED-based light source of the illumination system may be configured to emit light towards a sample 150 to be observed via the microscope 130. Optionally, as further shown in FIG. 1b, the microscope system 100 may comprise the system 140. The surgical microscope system 100 shown in FIG. 1b comprises a number of optional components, such as a base unit 105 (comprising the system 140) with a (rolling) stand, one or more displays 160, a (robotic or manual) arm 170 which holds the microscope 130 in place, and which is coupled to the base unit 105 and to the microscope 130, and steering handles 180 that are attached to the microscope 130. One or more of the displays 160 may be part of the microscope 130, e.g. as auxiliary or as ocular displays. In the context of this application, the term "(surgical) microscope system" is used, in order to cover the portions of the system that are not part of the actual microscope (which comprises optical components), but which are used in conjunction with the microscope, such as the display or an illumination system.

More details and aspects of the illumination system 110, the system 140 and/or the microscope system 100 are mentioned in connection with the proposed concept or one or more examples described above or below (e.g. FIGS. 2 to 5). The illumination system 110, the system 140 and/or the microscope system 100 may comprise one or more additional optional features corresponding to one or more aspects of the proposed concept or one or more examples described above or below.

Figure 2:
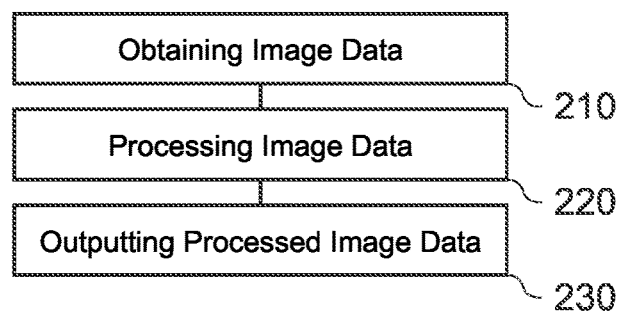
FIG. 2 shows a flow chart of a method for a microscope.

FIG. 2 shows a flow chart of a corresponding method for a microscope. For example, the method may be suitable for the microscope 130, and/or the microscope system 100, of FIGS. 1a and/or 1b. The method comprises obtaining 210 image data of an optical imaging sensor of the microscope. The image data represents light reflected by a sample that is illuminated by one or more LED-based light sources. The light emitted by the one or more LED-based light sources is filtered such that light having a wavelength that coincides with at least one fluorescence emission wavelength of at least one fluorescent material is attenuated or blocked. In other words, the image data may represent light across a spectrum, with a portion of the spectrum that that coincides with at least one fluorescence emission wavelength of at least one fluorescent material being attenuated or blocked. The method comprises processing 220 the image data to generate processed image data. A portion of the processed image data representing light having a wavelength that coincides with the at least one fluorescence emission wavelength of the at least one fluorescent material is generated based on the image data. The method comprises outputting 230 the processed image data.

As indicated above, features described in connection with the system 140, the illumination system 110, the microscope 130 and the microscope system 100 of FIGS. 1a and/or 1b may be likewise applied to the method of FIG. 2.

More details and aspects of the method are mentioned in connection with the proposed concept or one or more examples described above or below (e.g. FIG. 1a to 1b, 3a to 5). The method may comprise one or more additional optional features corresponding to one or more aspects of the proposed concept or one or more examples described above or below.

Embodiments of the present disclosure provide an illumination that is based on several LED chips. Each chip may be combined with a TIR based compound parabolic concentrator (CPC). The (LED) chips may emit different spectral ranges and may be controlled independently. Embodiment of the present disclosure thus provide LED-based illumination for a microscope.

Embodiments may use separate light sources on the microscope entrance side, which emit different spectra and their power can be controlled individually. This allows to control the brightness of the image as well as the fluorescence power independently and further helps controlling shadows in the white light mode. Due to its redundant layout, the illumination may still work, even if one of the LEDs fails.

FIGS. 3a and 3b show schematic diagrams of embodiments of a microscope system. FIGS. 3a and 3b show a placement of LED-based light sources 112, 116 and 118 of the illumination system 110 relative to an objective 134 of a microscope 130. FIG. 3a shows a view of a microscope front, and FIG. 3b shows a sectional view thereof. Each of the LED-based light source of the illumination system is configured to emit light towards a sample to be observed via the microscope, and each LED-based light source is arranged in adjacent to the objective 134 of the microscope 130. For example, the LED-based light sources may be arranged at (i.e. adjacent to) an entrance of the objective that is directed at the sample to be observed via the microscope, e.g. at a downward-facing entrance of the objective. For example, each LED-based light source may be arranged such, that the light emitted by the light source is emitted at least in parallel to a light path of the microscope that traverses the objective of the microscope. For example, the one or more first and the one or more second (and optionally the one or more third) LED-based light sources may be arranged at a side of the microscope facing towards the sample (also denoted "entrance side") of the microscope.

As has been introduced above, multiple light sources of each of the groups or sets light sources may be included in the illumination system. For example, the illumination system may comprise two or more first LED-based light sources and two or more second LED-based light sources (and, optionally, two or more third LED-based light sources). In FIGS. 3a and 3b, an example is shown where two first LED-based light sources, six second LED-based light sources and two third LED-based light sources are used. The light sources of each group or set may be arranged at either side of an objective 134 of the microscope 130. For example, the respective sides may be opposing sides relative to the objective 134 of the microscope.

In FIGS. 3a and 3b, the placement of the at least one optical filter 114 (in front of the one or more first LED-based light sources) and of the at least one second optical filter 122 (in front of four of the second LED-based light sources at the edges of the array of light sources) is shown. Additionally, in FIG. 3b, the arrangement of the CPCs relative to the LED-based light sources is shown.

As shown in FIGS. 3a and 3b, an (one-dimensional) array of combinations of LED-CPC (LED-based light source plus Compound Parabolic Concentrator) may be placed sideways along the objective. Some LED-CPC combination (i.e. the first LED-based light sources) have a band pass filter (i.e. the at least one optical filter) for a defined control of the emitted spectrum. In the example shown in FIGS. 3a and 3b, Five LED-CPCs are placed on each side of the objective. Two of these LEDs have a spectrum across the visible range (white light LED), i.e. the one or more first LED-based light sources 112. One LED emits a spectrum with a peak at 405 nm, one LED with a peak at 480 nm, one LED with a peak at 788 nm (i.e. the one or more second LED-based light sources 116). In front of one of the white light LEDs an additional band pass filter is placed (e.g. the band-pass filter of FIG. 4), which blocks the fluorescence emissions of two fluorescent materials. Two band pass filters are placed in front of the 480 nm and 788 nm LED.

More details and aspects of the illumination system and microscope system are mentioned in connection with the proposed concept or one or more examples described above or below (e.g. FIG. 1a to 2, 4 to 5). The illumination system and microscope system may comprise one or more additional optional features corresponding to one or more aspects of the proposed concept or one or more examples described above or below.

FIG. 4 shows a diagram of a transmission of a band pass filter for filtering white light. On the x-axis, the wavelength in nm is shown, on the y-axis, the transmission in % is shown. For example, the shown filter may be used to implement the at least one optical filter 114 of FIGS. 1a to 3b. As shown in FIG. 4, the filter may block or attenuate light in the range between 490 nm and 560 nm, and between 610 nm and 660 nm wavelength.

More details and aspects of the bandpass filter are mentioned in connection with the proposed concept or one or more examples described above or below (e.g. FIG. 1a to 3b, 5). The band-pass filter may comprise one or more additional optional features corresponding to one or more aspects of the proposed concept or one or more examples described above or below.

Figure 5:
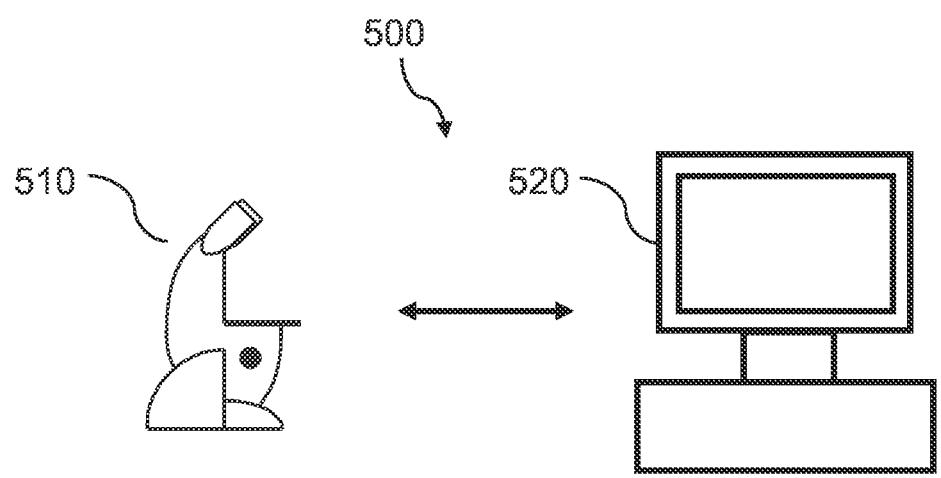
FIG. 5 shows a schematic diagram of a microscope system comprising a microscope and a computer system.

Some embodiments relate to a microscope comprising a system as described in connection with one or more of the FIGS. 1 to 4. Alternatively, a microscope may be part of or connected to a system as described in connection with one or more of the FIGS. 1 to 4. FIG. 5 shows a schematic illustration of a (microscope) system 500 configured to perform a method described herein. The system 500 comprises a microscope 510 and a computer system 520. The microscope 510 is configured to take images and is connected to the computer system 520. The computer system 520 is configured to execute at least a part of a method described herein. The computer system 520 may be configured to execute a machine learning algorithm. The computer system 520 and microscope 510 may be separate entities but can also be integrated together in one common housing. The computer system 520 may be part of a central processing system of the microscope 510 and/or the computer system 520 may be part of a subcomponent of the microscope 510, such as a sensor, an actor, a camera or an illumination unit, etc. of the microscope 510.

The computer system 520 may be a local computer device (e.g. personal computer, laptop, tablet computer or mobile phone) with one or more processors and one or more storage devices or may be a distributed computer system (e.g. a cloud computing system with one or more processors and one or more storage devices distributed at various locations, for example, at a local client and/or one or more remote server farms and/or data centers). The computer system 520 may comprise any circuit or combination of circuits. In one embodiment, the computer system 520 may include one or more processors which can be of any type. As used herein, processor may mean any type of computational circuit, such as but not limited to a microprocessor, a microcontroller, a complex instruction set computing (CISC) microprocessor, a reduced instruction set computing (RISC) microprocessor, a very long instruction word (VLIW) microprocessor, a graphics processor, a digital signal processor (DSP), multiple core processor, a field programmable gate array (FPGA), for example, of a microscope or a microscope component (e.g. camera) or any other type of processor or processing circuit. Other types of circuits that may be included in the computer system 520 may be a custom circuit, an application-specific integrated circuit (ASIC), or the like, such as, for example, one or more circuits (such as a communication circuit) for use in wireless devices like mobile telephones, tablet computers, laptop computers, two-way radios, and similar electronic systems. The computer system 520 may include one or more storage devices, which may include one or more memory elements suitable to the particular application, such as a main memory in the form of random access memory (RAM), one or more hard drives, and/or one or more drives that handle removable media such as compact disks (CD), flash memory cards, digital video disk (DVD), and the like. The computer system 520 may also include a display device, one or more speakers, and a keyboard and/or controller, which can include a mouse, trackball, touch screen, voice-recognition device, or any other device that permits a system user to input information into and receive information from the computer system 520.

Some or all of the method steps may be executed by (or using) a hardware apparatus, like for example, a processor, a microprocessor, a programmable computer or an electronic circuit. In some embodiments, some one or more of the most important method steps may be executed by such an apparatus.

Depending on certain implementation requirements, embodiments of the invention can be implemented in hardware or in software. The implementation can be performed using a non-transitory storage medium such as a digital storage medium, for example a floppy disc, a DVD, a Blu-Ray, a CD, a ROM, a PROM, and EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may, for example, be stored on a machine readable carrier.

Other embodiments comprise the computer program for performing one of the methods described herein, stored on a machine readable carrier.

In other words, an embodiment of the present invention is, therefore, a computer program having a program code for performing one of the methods described herein, when the computer program runs on a computer.

A further embodiment of the present invention is, therefore, a storage medium (or a data carrier, or a computer-readable medium) comprising, stored thereon, the computer program for performing one of the methods described herein when it is performed by a processor. The data carrier, the digital storage medium or the recorded medium are typically tangible and/or non-transitionary. A further embodiment of the present invention is an apparatus as described herein comprising a processor and the storage medium.

A further embodiment of the invention is, therefore, a data stream or a sequence of signals representing the computer program for performing one of the methods described herein. The data stream or the sequence of signals may, for example, be configured to be transferred via a data communication connection, for example, via the internet.

A further embodiment comprises a processing means, for example, a computer or a programmable logic device, configured to, or adapted to, perform one of the methods described herein.

A further embodiment comprises a computer having installed thereon the computer program for performing one of the methods described herein.

A further embodiment according to the invention comprises an apparatus or a system configured to transfer (for example, electronically or optically) a computer program for performing one of the methods described herein to a receiver. The receiver may, for example, be a computer, a mobile device, a memory device or the like. The apparatus or system may, for example, comprise a file server for transferring the computer program to the receiver.

In some embodiments, a programmable logic device (for example, a field programmable gate array) may be used to perform some or all of the functionalities of the methods described herein. In some embodiments, a field programmable gate array may cooperate with a microprocessor in order to perform one of the methods described herein. Generally, the methods are preferably performed by any hardware apparatus.

As used herein the term "and/or" includes any and all combinations of one or more of the associated listed items and may be abbreviated as "/".

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus.

LIST OF REFERENCE SIGNS

100 Microscope system
105 Base unit
110 Illumination system
112 One or more first light sources
114 Optical filter
116 One or more first light sources
118 One or more third light sources
120 Optical concentration element
122 Second optical filter
130 Microscope
132 Optical imaging sensor
134 Objective
140 System
142 Interface
144 One or more processors
146 One or more storage devices
150 Sample
160 Display
170 Arm
180 Handles
210 Obtaining image data
220 Processing the image data
230 Outputting the processed image data
500 Microscope system
510 Microscope
520 Computer system

The invention claimed is:

1. A microscope system comprising a microscope and a Light-Emitting Diode (LED)-based illumination system for the microscope, the microscope comprising an objective, wherein the objective comprises a first side and a second side, the illumination system comprising:
   a plurality of first LED-based light sources, wherein the plurality of first LED-based light sources are configured to emit light across a white light color spectrum;
   at least one optical filter, wherein the at least one optical filter is arranged to filter the light emitted by the plurality of first LED-based light sources;
   a plurality of second LED-based light sources, wherein the plurality of second LED-based light sources are configured to provide light having at least one peak at a wavelength that is tuned to an excitation wavelength of at least one fluorescent material,
   wherein each LED-based light source of the illumination system is configured to emit light towards a sample to be observed via the microscope,
   wherein each LED-based light source is arranged adjacent to an entrance of the objective of the microscope,
   wherein at least one of the plurality of first LED-based light sources and at least one of the plurality of second LED-based light sources is arranged at the first side of the objective,
   wherein at least one of the plurality of first LED-based light sources and at least one of the plurality of second LED-based light sources is arranged at the second side of the objective, and
   wherein the arrangement of the first and second LED-based light sources on the first and second side of the objective is linear.

2. The microscope system according to claim 1, wherein the plurality of second LED-based light sources are configured to emit light having a peak at one or more of
   between 390 nm and 420 nm,
   between 460 nm and 500 nm, and
   between 780 nm and 810 nm.

3. The microscope system according to claim 1, wherein the at least one optical filter is configured to attenuate or block light having a wavelength that coincides with at least one fluorescence emission wavelength of the at least one fluorescent material.

4. The microscope system according to claim 1, further comprising one or more third LED-based light sources, wherein the one or more third LED-based light sources are configured to emit light across the white light color spectrum.

5. The microscope system according to claim 1, wherein at least a subset of the plurality of second LED-based light sources are configured to provide light having at least one peak at a wavelength that is tuned to an excitation wavelength of the at least one fluorescent material without using a filter to limit the emitted light to the at least one peak.

6. The microscope system according to claim 1, further comprising at least one second optical filter, arranged to filter the light emitted by at least a subset of the plurality of second LED-based light sources.

7. The microscope system according to claim 1, comprising one or more processors configured to control the plurality of first and the plurality of second LED-based light sources independent from each other.

8. The microscope system according to claim 1, wherein each LED-based light source is configured to emit light towards a sample to be observed via the microscope, wherein each LED-based light source is configured to emit the light towards the sample through an optical concentration element.

9. The microscope system according to claim 8, wherein the optical concentration element is a compound parabolic concentrator.

10. The microscope system according to claim 1, comprising one or more processors and one or more storage devices, wherein the system is configured to:
obtain image data of an optical imaging sensor of the microscope,
wherein the image data represents light reflected by the sample that is illuminated by the plurality of first and second LED-based light sources, wherein the light emitted by the plurality of first LED-based light sources is filtered such that light having a wavelength that coincides with at least one fluorescence emission wavelength of the at least one fluorescent material is attenuated or blocked;
process the image data to generate processed image data, wherein a portion of the processed image data representing light having a wavelength that coincides with the at least one fluorescence emission wavelength of the at least one fluorescent material is generated based on the image data; and
output the processed image data.

11. The microscope system according to claim 10, wherein the image data represents light reflected by the sample that is illuminated by the plurality of first LED-based light sources of the illumination system.

12. A method for the microscope system of claim 1, the method comprising:
obtaining image data of an optical imaging sensor of the microscope,
wherein the image data represents light reflected by a sample that is illuminated by the plurality of first and second LED-based light sources, wherein the light emitted by the plurality of first LED-based light sources is filtered such that light having a wavelength that coincides with at least one fluorescence emission wavelength of at least one fluorescent material is attenuated or blocked;
processing the image data to generate processed image data, wherein a portion of the processed image data represents the attenuated or blocked light having a wavelength that coincides with the at least one fluorescence emission wavelength of the at least one fluorescent material is generated based on the image data; and
outputting the processed image data.

13. A non-transitory, computer-readable medium comprising a program code for performing a method for the microscope system of claim 1, when the program code is executed on a processor, the method comprising:
obtaining image data of an optical imaging sensor of the microscope,
wherein the image data represents light reflected by a sample that is illuminated by the plurality of first and second LED-based light sources, wherein the light emitted by the plurality of first LED-based light sources is filtered such that light having a wavelength that coincides with at least one fluorescence emission wavelength of at least one fluorescent material is attenuated or blocked;
processing the image data to generate processed image data, wherein a portion of the processed image data represents the attenuated or blocked light having a wavelength that coincides with the at least one fluorescence emission wavelength of the at least one fluorescent material is generated based on the image data; and
outputting the processed image data.

14. The microscope system of claim 1, wherein the linear arrangement of the first and second LED-based light sources on the first side of the objective is parallel to the linear arrangement of the first and second LED-based light sources on the second side of the objective.

* * * * *